United States Patent [19]

Hersh et al.

[11] Patent Number: 4,777,048

[45] Date of Patent: Oct. 11, 1988

[54] PHARMACEUTICAL COMPOSITION CONTAINING A LIQUID LUBRICANT

[75] Inventors: Marvin Hersh, Strafford; Charles W. Lentine, Brookhaven, both of Pa.

[73] Assignee: American Home Products Corporation, New York, N.Y.

[21] Appl. No.: 886,699

[22] Filed: Jul. 18, 1986

Related U.S. Application Data

[60] Division of Ser. No. 730,232, May 3, 1985, Pat. No. 4,620,974, which is a continuation-in-part of Ser. No. 511,801, Jul. 7, 1983, abandoned.

[51] Int. Cl.$^4$ ............................................. A61K 9/48
[52] U.S. Cl. .................................. 424/452; 53/266 R
[58] Field of Search ........................... 424/452; 53/266

[56] References Cited

U.S. PATENT DOCUMENTS

| | | | |
|---|---|---|---|
| 2,830,010 | 4/1958 | Valentine et al. | 424/37 |
| 2,870,062 | 1/1959 | Stanley et al. | 424/37 |
| 2,889,252 | 6/1959 | Valentine et al. | 424/37 |
| 2,899,361 | 8/1959 | McMillion | 424/37 |
| 3,374,146 | 3/1968 | Blicharz et al. | 424/452 |
| 3,421,282 | 1/1969 | Hasekawa et al. | 424/452 |
| 3,632,742 | 1/1972 | Eckert et al. | 424/37 |
| 3,780,195 | 12/1973 | Balassa | 424/37 |
| 3,784,684 | 1/1974 | Bossert et al. | 424/37 |
| 3,859,431 | 1/1975 | Newton et al. | 424/37 |
| 3,862,311 | 1/1975 | Leeson | 424/452 |
| 3,867,521 | 2/1975 | Miskel et al. | 424/37 |
| 3,927,196 | 12/1975 | Hersh | 424/452 |
| 4,002,718 | 1/1977 | Gardella et al. | 424/37 |
| 4,088,750 | 5/1978 | Cresswell et al. | 424/37 |
| 4,198,391 | 4/1980 | Grainger | 424/37 |
| 4,343,789 | 8/1982 | Kawata et al. | 424/78 |
| 4,366,145 | 12/1982 | Stoopak et al. | 424/37 |
| 4,406,879 | 9/1983 | Miyazaki et al. | 424/14 |
| 4,497,158 | 2/1985 | Durr et al. | 424/452 |
| 4,620,974 | 11/1986 | Hersh et al. | 424/452 |

FOREIGN PATENT DOCUMENTS

| | | | |
|---|---|---|---|
| 0049909 | 4/1982 | European Pat. Off. | 424/37 |
| 2064321A | 6/1981 | United Kingdom . | |

OTHER PUBLICATIONS

Samyn et al., J. Pharm. Sci. 59, 169, (1970).
Iranloye et al., J. Pharm. Sci. 67, 535, (1978).
Levy et al., J. Pharm. Sci. 52, 1139, (1963).
Lachman et al., Theory and Practice of Industrial Pharmacy, 2nd Ed., pp. 108–109.
Chiou et al., J. Pharm. Sci. 65, 1702, (1976).
Lerk et al., J. Pharm. Sci. 67, 935,(1978).
Goodhart et al., J. Pharm. Sci. 62, 304, (1973).
Short et al., J. Pharm. Sci. 61, 1733, (1972).
Geneidi et al., J. Pharm. Sci. 67, 114 (1978).

*Primary Examiner*—Shep K. Rose
*Attorney, Agent, or Firm*—Richard K. Jackson

[57] ABSTRACT

Pharmaceutical compositions produced with liquid, hydrophilic lubricants possessing markedly improved dissolution rates.

3 Claims, No Drawings

PHARMACEUTICAL COMPOSITION CONTAINING A LIQUID LUBRICANT

This is a division of application Ser. No. 730,232, filed 5-3-85, now U.S. Pat. No. 4,620,974, which is a continuation-in-part of Ser. No. 511,801 filed 7-7-83, now abandoned.

BACKGROUND OF THE INVENTION

Solid, hydrophobic lubricants continue to be currently used in the pharmaceutical art of tableting and filling of hard gelatin capsules even though it is known that the use of hydrophobic lubricants such as magnesium stearate diminish dissolution rates, and consequently could possibly reduce absorption rates, of the dosage formulation. Diminished dissolution rates of several capsule formulations with increases of magnesium stearate concentration were disclosed by Samyn and Jung, J. Pharm. Sci. 59, 169 (1970). Iranloye et al., J. Pharm. Sci. 67, 535 (1978), studied the effects of concentration of hydrophobic lubricants (calcium stearate, glyceryl monostearate, magnesium stearate, stearic acid and talc) on the dissolution rate of salicylic acid, aspirin and equimolar mixtures thereof and reported decreased dissolution rates with increased concentration of each lubricant other than talc. The authors concluded that, if hydrophobic lubricants slow dissolution, highly water-soluble lubricants might enhance dissolution. However, polyethylene glycol 4000 failed to affect dissolution at concentrations as high as 5 percent, leading the authors to speculate that the lubricant must simultaneously be water-soluble and surface active to enhance dissolution. Levy et al., J. Pharm. Sci. 52, 1139 (1963), had previously shown that sodium lauryl sulfate increased dissolution rates of salicylic acid over that of magnesium stearate in compressed tablets.

The use of surfactants in pharmaceutical formulations to assist in disintegration and dissolution of drug material is well known. Lachman et al., *Theory and Practice of Industrial Pharmacy*, Second Edition, pp. 108-9, disclose the use of surface active agents or surfactants in almost every dosage form including liquids, semi-solids and solids. The surface active agents play an important role in the absorption and efficacy of certain drugs. The nature of this role is quite obscure. Both enhancement of absorption and retardation of drug absorption have been credited to the presence of surface active agents. It cannot always be determined whether the function of a surfactant is to alter solubility, dissolution rates, and/or absorbability of the drug based upon its action on the drug itself or on a semi-permeable membrane within the host body. Similarly, whether the formation of micelle units and their polar/non-polar molecule orientation is critical to the function of the surfactants is not readily ascertainable.

Chiou et al., J. Pharm. Sci. 65, 1702 (1976), disclose enhanced dissolution rates for poorly water soluble drugs by crystallization from an aqueous surfactant solution. Polysorbate 80 (Tween 80) was employed in 2.5% aqueous solution for the purpose of drug precipitation.

Lerk et al., J. Pharm. Sci. 67, 935 (1978), disclose hydrophilic coating of hydrophobic drug particles to enhance wetting and dissolution. Hersh, U.S. Pat. No. 3,927,196, had shown earlier that a hydrophobic lubricant could be coated with a hydrophilic material to enhance dissolution of a therapeutic composition containing the lubricant.

Goodhart et al., J. Pharm. Sci. 62, 304 (1973), disclose a method for testing tablet and capsule dissolution rates. The authors note that previous studies have demonstrated prolonged disintegration/dissolution times with an increase in the level of magnesium stearate which is the standard lubricant employed in hard gelatin capsule formulations. The magnesium stearate in effect waterproofs the contents of a hard gelatin capsule. The authors noted on page 308, that the addition of a surfactant such as sodium lauryl sulfate improved disintegration of the capsules when tested in artificial gastric fluid without enzymes.

Short et al., J. Pharm. Sci. 61, 1733 (1972), disclose the dissolution of hydrocortisone in a number of systems containing an N-alkylpolyoxyethylene surfactant.

U.S. Pat. No. 3,862,311 granted Jan. 21, 1975, to Leeson, discloses the use of various types of surfactants in conjunction with polyethylene glycol carriers for assistance in dissolution and absorption of compositions containing progesterone. The preferred surfactants are non-ionics.

Geneidi et al., J. Pharm. Sci. 67, 114 (1978), disclose the theoretical relationship between enhancement of dissolution rate of a drug and its GI absorption rate.

DESCRIPTION OF THE INVENTION

In accordance with this invention, there is provided a solid pharmaceutical composition of matter comprising a therapeutic agent in intimate admixture with a non-solubilizing quantity of a pharmaceutically-acceptable, liquid, hydrophilic lubricant. The solid pharmaceutical composition is especially suitable for filling hard gelatin capsules. This invention also provides an improved method for filling hard gelatin capsules with solid pharmaceutical compositions containing a therapeutic agent and a lubricant wherein said lubricant is a pharmaceutically acceptable, liquid, hydrophilic lubricant. The hard gelatin, telescoping two-piece cap and body capsule filled with the solid pharmaceutical composition containing a pharmaceutically acceptable, liquid, hydrophilic lubricant represents an additional aspect of the invention as does the method for providing lubrication to a solid pharmaceutical composition and the method for improving the dissolution rate of therapeutic agents from hard gelatin capsules by incorporating a pharmaceutically acceptable, liquid, hydrophilic lubricant into the pharmaceeutical composition containing said therapeutic agent.

By the term "non-solubilizing" used to modify the liquid, hydrophilic lubricant, applicant means that the liquid lubricant is not employed as a solvent to dissolve either the active therapeutic agent or any or all of the materials combined to produce the solid pharmaceutical composition.

The liquid, hydrophilic lubricant employed in the pharmaceutical compositions of this invention functions as a classical solid, hydrophobic lubricant in as much as it provides for proper flow characteristics of the dry composition when filling a hard gelatin capsule body [Reier et al., J. Pharm. Sci. 57, 660 (1968)], prevents binding of the rotary auger in the powder filled hopper [C. Lindenwald, Pharm. Ind. 28, 614 (1965)] employed in filling hard gelatin capsules and permits smooth telescoping closure of the filled capsule body part into the cap, while not reducing the friction between the capsule halves to the point where they will easily separate upon further manipulation.

In addition, the use of a liquid as the lubricaant markedly reduces the production of dust which conventionally attends the filling of capsules and preparation of pharmaceutical powder mixes. The reduction of atmospheric dust is of great value in the handling of tranquilizers, barbiturates, analgesics, antibiotics, antihypertensives, antiinflammatory agents, steroids (hormones), etc., which may cause contact dermatitis or induce systemic effects upon inhalation by workers. When using a liquid lubricant, the reduction in dust is such that it is no longer necessary to polish hard gelatin capsules after filling.

Furthermore, the liquid lubricant provides an ideal medium for inclusion, by solution, suspension or emulsion, of surfactants, low level actives or other adjuvants which are desireably made as homogeneous as possible in a solid pharmaceutical formulation. And, the liquid lubricant present in a hard gelatin capsule tends to reduce aging (hardening of the gelatin capsule via further polymerization) which results in lower dissolution rates.

The liquid, hydrophilic lubricants which may be employed in various pharmaceutical formulations include polyalkylene glycols of molecular weight between about 200 and about 900, such as, polyethylene glycol and polypropylene glycol; glycerin, propylene glycol, and liquid polyhydric alcohol fatty acid esters (e.g. Glycomul ® or Glycosperse ®). Each of these lubricants pose unique problems which might dictate against their use in a specific application. For example, glycerin and propylene glycol are so hygroscopic that they may cause physical and chemical problems with the pharmaceutical. The more viscous Glycosperse ® tends to coat the external lip portion of a hard capsule body and provide such a frictionless binding that the capsules tend to separate on handling. Hence, the preferred liquid lubricants are the polyethylene glycols of molecular weight from about 200 to about 900. The most preferred liquid lubricant is polyethylene glycol having a molecular weight range of from about 380 to about 420 (PEG 400). These lubricants exert some level of surface activity in addition to lubrication and otherwise appear to be ideally suited for use in production of solid pharmaceutical compositions for hard gelatin capsule filling.

In addition, this invention provides solid pharmaceutical compositions comprising a therapeutic agent in intimate admixture with a pharmaceutically acceptable, liquid, hydrophilic lubricant and a surface active agent. The surfactant further improves the dissolution rate by reducing the surface tension at the liquid-solid interface crated between the pharmaceutical composition and fluid dissolving the composition. Thus, the hydrophilicity of the liquid lubricant aids in drawing water into the matrix of the tablet or capsule while the surface active agent improves the wettability of the solid material to afford, in concert, a markedly improved dissolution rate. Typical surfactants which are incorporated into the pharmaceutical compositions of this invention are cationic, anionic and nonionic surface active agents well-known in the art, such as, the fatty esters of polyoxyethylene sorbitan (Tween series 20 to 85, ICI, United States), a polyoxyethylene condensate of a hydrophobic base formed by polymerization of propylene oxide and propylene glycol (Pluronic or Poloxamer series, BASF Wyandotte Chemical Co.), sorbitan monolaurate (Span 20, ICI United States), octyl- phenoxy polyethoxy ethanol (Triton X, Rohm and Haas), cetylpyridinium chloride, dioctyl sodium sulfosuccinate, and the like.

The quantity of liquid, hydrophilic lubricant and surfactant employed in the manufacture of the pharmaceutical compositions of this invention may vary greatly depending upon the characteristics of the therapeutic agent and other capsule adjuvants employed. The optimum quantity of either or both is, however, readily determined by empirical investigation. For example, a series of incremental 5 percent increases of PEG 400 admixed with the conventional formulation containing oxazepam as presented in Example 1, infra, demonstrated a maximum useful concentration of lubricant at about 25 percent by weight, at which point the formulation was clumpy and would not run in automatic or semi-automatic fillers. Adjustment of the quantity of liquid lubricant and surfactant to provide 75 percent or better dissolution in forty-five minutes is also readily achieved by empirical investigation of in vitro dissolution rates.

The therapeutic agent contemplated for use in the novel pharmaceutical compositions of this invention is any known solid therapeutic agent adaptable for administration via a hard gelatin capsule. In general, the combination of a pharmaceutically acceptable liquid lubricant and surfactant is employed with greatest advantage for the purpose of dramatically improving the dissolution rate of poorly soluble therapeutic agents including tranquilizers, barbiturates, analgesics, antibiotics, antihypertensives, antiinflammatories, hormonal steroids, and the like, which exhibit slow in vitro availability rates. Dissolution enhancement of the compositions of this invention containing the poorly soluble active pharmaceutical is further optimized after inclusion of the lubricant-surfactant combination by achieving maximum distribution of the lubricant-surfactant combination via milling or screening to reduce agglomerates of loosely adhering particles. Multiple milling or screening may enhance the dissolution rate, depending upon the efficiency of the initial agglomerated particle disruption.

Oxazepam is employed as the therapeutic agent in the following examples of therapeutic compositions for filling hard gelatin capsules because it is a good example of a compound with a slow dissolution rate. It is to be understood that the invention is not limited to use with oxazepam or drugs which are relatively insoluble. The use of a liquid, hydrophilic lubricant-surfactant, with or without the addition of an additional surface active agent, serves to increase the dissolution rate of tableted and hard encapsulated pharmaceutical compositions which are customarily and presently formulated with solid hydrophobic lubricants such as magnesium stearate, talc, or stearic acid, even when the drug itself is readily soluble in vitro and in vivo.

In each of the following formulations employed to illustrate the typical improvement in dissolution rates achieved with this invention, the solid ingredients consisting of the active material (oxazepam) and tablet excipients (lactose and croscarmellose) are first mixed in a suitable mixer. The liquid ingredients consisting of the lubricant (PEG 400) and surfactant (Polysorbate 80) are combined and mixed with a suitable mixer. This combination is added slowly to the mixed powders and mixed to achieve adequate dispersion. This wetted material is passed through a No. 30 screen and then remixed to further homogeneous dispersal. In formulations where magnesium stearate is present, this solid hydrophobic lubricant is added through a fine screen to the mixed powders which are then thoroughly mixed. All components of these formulations are in milligrams.

chloric acid as dissolution medium. In actual practice, hard gelatin capsules filled with the pharmaceutical formulation of Example V, supra, provided bio-availability in vivo which was not statistically distinct with respect to rate and extent of absorption from com-

| DISSOLUTION RATES OF HARD GELATIN CAPSULES | | | | | |
|---|---|---|---|---|---|
| | | | Example No. | | |
| | I (Conventional) | II (Reduced Magnesium Stearate) | III (No Magnesium Stearate) | IV (PEG and No Magnesium Stearate) | V (PEG and Polysorbate) |
| Oxazepam | 30 | 30 | 30 | 30 | 30 |
| Lactose USP | 182 | 182 | 147 | 182 | 182 |
| Croscarmellose Sodium, NF | — | 6.6 | 7.4 | 6.6 | 6.6 |
| PEG 400 NF | — | — | — | 3.3 | 3.3 |
| Polysorbate 80 NF | — | — | — | — | 1.1 |
| Magnesium Stearate NF | 6.6 | 1.1 | — | — | — |
| % dissolved in 30'* | 2–5 | 45–59 | 15–22 | 57–77 | 85–95 |

*Using apparatus described in U.S.P. XX - N.F. XV (1980)(711) p. 959, with chemically assayed values.

As may be readily seen, the dissolution rate is markedly improved in Formula II by merely reducing the quantity of solid hydrophobic lubricant (magnesium stearate) and adding an internally cross-linked carboxymethylcellulose sodium salt disintegrant (croscarmellose sodium). The results obtained from Formula III demonstrate that the addition of a disintegrant alone with exclusion of a lubricant is not the answer to the problem. Dissolution of Formula IV demonstrates a marked improvement resulting from the addition of a liquid, hydrophilic, low molecular weight polyethylene glycol (PEG 400) which acts as a lubricant and weak surfactant. Upon addition of a minor amount of another surfactant (Polysorbate 80) the thirty minute in vitro dissolution rate is improved to between 85 to 95 percent of the composition dosage. This exceeds the desired in vitro dissolution rate of not less than 75 percent in forty-five minutes currently propounded by the U.S.P. XX—N.F. XV, 1980, as desireable.

Other surface active agents work similarly well with the liquid, hydrophilic lubricant to afford rapid dissolution of the pharmaceutical compositions as may be seen in the following examples:

| | Example No. | | | |
|---|---|---|---|---|
| | VI PEG & Sorbitan Mono-laurate | VII PEG & Triton | VIII PEG & Cetylpyrid. | IX PEG & DSS* |
| Oxazepam, mg | 30 | 30 | 30 | 30 |
| Lactose USP | 147.1 | 147.1 | 147.1 | 182 |
| Croscarmellose Sodium, USP | 6.6 | 6.6 | 6.6 | 6.6 |
| PEG 400, NF | 1.1 | 1.1 | 1.1 | 1.1 |
| Triton X-100 | — | 0.185 | — | — |
| Cetylpyridinium Chloride | — | — | 0.185 | — |
| Sorbitan monolaurate | 0.185 | — | — | — |
| Dioctyl Sodium Sulfosuccinate* | — | — | — | 0.26 |
| Magnesium Stearate, USP | — | — | — | — |
| % dissolved in 30 | 91 | 96 | 86 | 93 |

All of the in vitro dissolution studies which produced the data reported above were run by the method described in U.S.P. XX, N.F. XV, 1980, using 0.1N hydropressed tablets now employed in the trade, a very desireable but difficult result to achieve with any given drug. Thus, a typical pharmaceutical formulation employing oxazepam as the active ingredient contains from about 10 to about 30 milligrams oxazepam; 0.5 to about 25 weight percent of composition of liquid polyalkylene glycol of molecular weight from about 200 to about 900; about 0.1 to about 25 weight percent of composition of surfactant, plus a filler.

The preferred formulations for oxazepam to be employed in filling hard gelatin capsules contain from about 10 to about 30 milligrams oxazepam, about 3 to about 11 weight percent ratio to active of polyethylene glycol lubricant of molecular weight from about 380 to 420, about 0.5 to about 2.5 weight percent ratio to active of nonionic surfactant, made up with filler and/or adjuvant(s) to provide a unit dose of from about 165 to 205 milligrams.

Three specific examples of formulations for unit dosage administration via hard gelatin capsules, expressed in milligrams, are:

| Oxazepam, USP | 10 | 15 | 30 |
|---|---|---|---|
| Lactose, USP | 167 | 162 | 147 |
| Croscarmellose Sodium, NF | 6.6 | 6.6 | 6.6 |
| PEG 400, NF | 1.1 | 1.1 | 1.1 |
| Polysorbate 80, NF | 0.22 | 0.22 | 0.22 |

What is claimed is:

1. In a method for filling a hard gelatin, telescoping two-piece cap and body capsule with a dry, dust-producing, solid pharmaceutical composition containing a therapeutic agent, the improvement of reducing atmosphere dust which consists essentially of the step of incorporating into said pharmaceutical composition not more than an effective lubricating amount of a pharmaceutically acceptable, hydrophilic, dust-reducing, liquid polyalkylene glycol to provide proper flow characteristics to said composition.

2. In the method of claim 1, the improvement in which said polyalkylene glycol is polyethylene glycol of molecular weight from about 200 to about 900.

3. In a method for filling a hard gelatin, telescoping two-piece cap and body capsule with a dry, dust-producing, solid pharmaceutical composition containing a therapeutic agent, the improvment which comprises reducing atmospheric dusts produced during the capsule filling operation by incorporating into said pharmaceutical composition not more than an effective lubricating, dust-reducing amount of a pharmaceutically acceptable, hydrophilic, liquid polyethylene glycol of molecular weight from about 200 to about 900, said polyethylene glycol being incorporated into said composition in an amount from about 0.5 to about 25 weight percent of said composition.

* * * * *